(12) United States Patent
Solazzo et al.

(10) Patent No.: US 9,339,594 B2
(45) Date of Patent: May 17, 2016

(54) BLADDER EVACUATION SYSTEM

(71) Applicants: Anthony Solazzo, Watchung, NJ (US); Michael J. Vaillancourt, Chester, NJ (US)

(72) Inventors: Anthony Solazzo, Watchung, NJ (US); Michael J. Vaillancourt, Chester, NJ (US)

(*) Notice: Subject to any disclaimer, the term of this patent is extended or adjusted under 35 U.S.C. 154(b) by 382 days.

(21) Appl. No.: 13/915,127

(22) Filed: Jun. 11, 2013

(65) Prior Publication Data
US 2014/0364820 A1 Dec. 11, 2014

(51) Int. Cl.
*A61M 1/00* (2006.01)
*A61B 5/15* (2006.01)
*A61M 3/02* (2006.01)

(52) U.S. Cl.
CPC ............ *A61M 1/0009* (2013.01); *A61M 1/0056* (2013.01); *A61M 1/0062* (2013.01); *A61M 3/0229* (2013.01); *A61M 3/0262* (2013.01); *A61M 1/0001* (2013.01); *A61M 1/006* (2014.02); *A61M 2210/1085* (2013.01)

(58) Field of Classification Search
CPC .......................... A61M 1/0009; A61M 1/0001
See application file for complete search history.

(56) References Cited

U.S. PATENT DOCUMENTS

| 4,137,917 | A | * | 2/1979 | Cohen ................. A61M 5/3145 604/190 |
| 4,243,527 | A | * | 1/1981 | Leonard ........................ 210/785 |
| 4,391,274 | A | * | 7/1983 | Kagan ............................ 604/190 |
| 4,573,983 | A | * | 3/1986 | Annis ............................. 604/322 |
| 5,042,502 | A | * | 8/1991 | Guirguis ........................ 600/584 |
| 5,494,044 | A | * | 2/1996 | Sundberg ....................... 600/562 |
| 5,931,646 | A | * | 8/1999 | Nogawa et al. ............... 417/395 |
| 6,045,540 | A | * | 4/2000 | Cross ............................. 604/256 |
| 2001/0049486 | A1 | * | 12/2001 | Evans ................. A61M 1/3621 604/4.01 |
| 2007/0021774 | A1 | * | 1/2007 | Hogendijk ..... A61B 17/320758 606/200 |

* cited by examiner

*Primary Examiner* — Tatyana Zalukaeva
*Assistant Examiner* — Sara Sass
(74) *Attorney, Agent, or Firm* — Francis C. Hand; Carella, Byrne, Et Al

(57) ABSTRACT

The evacuation system employs a piston to deliver fluid for irrigating and aspirating a body cavity, such as a bladder. A pivotal screen is disposed across the flow path of the fluid to move out of the fluid flow path during irrigation of the bladder and to move back into the flow path during aspiration of the bladder. The screen screens out particulate matter from the return flow for depositing into the container of the system.

15 Claims, 6 Drawing Sheets

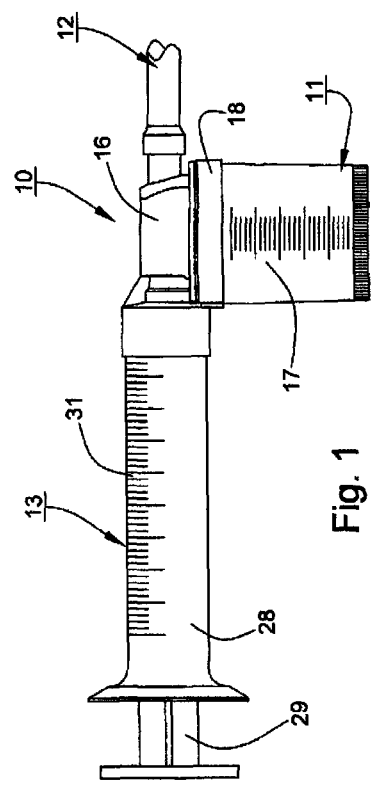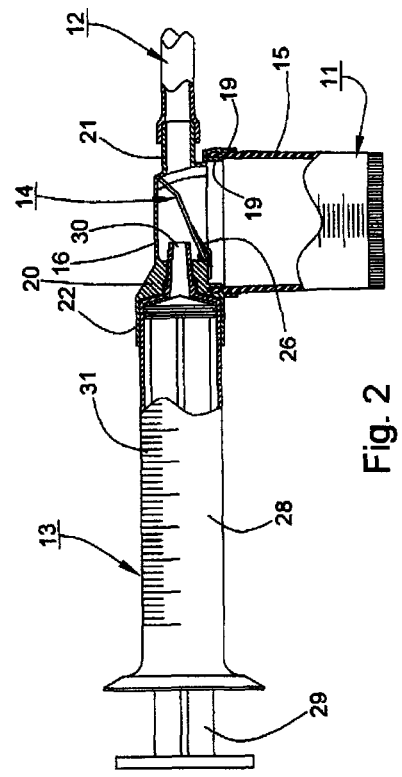

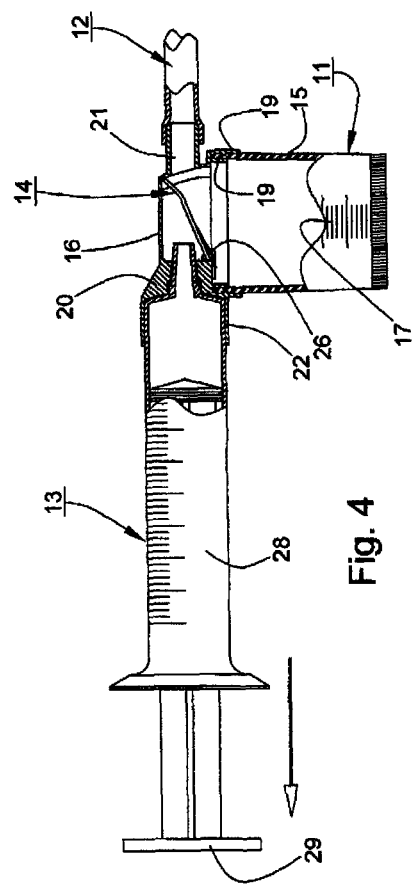
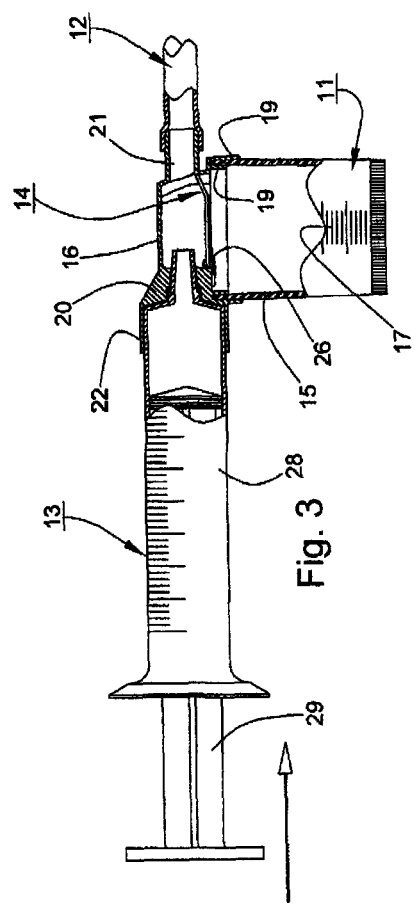

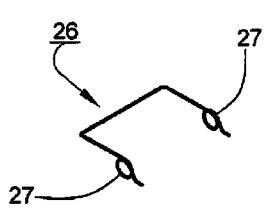
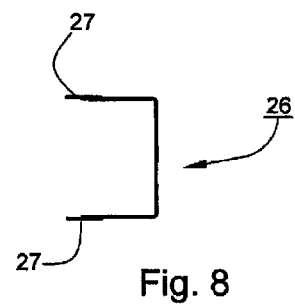
Fig. 7
Fig. 8
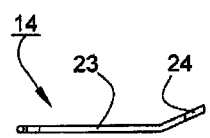
Fig. 6
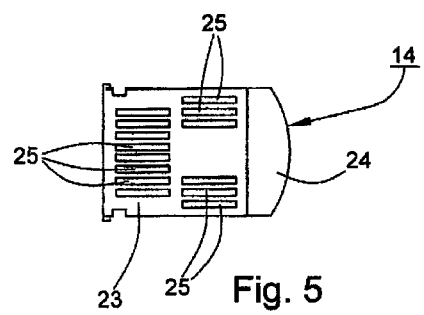
Fig. 5

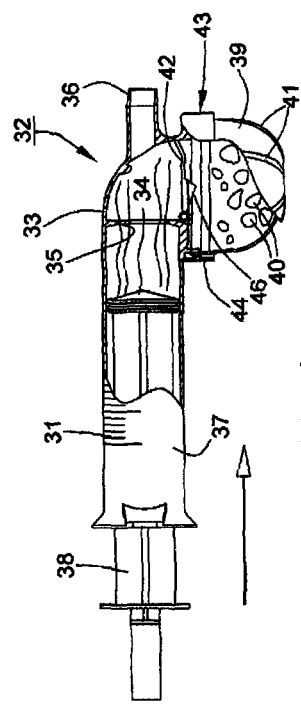
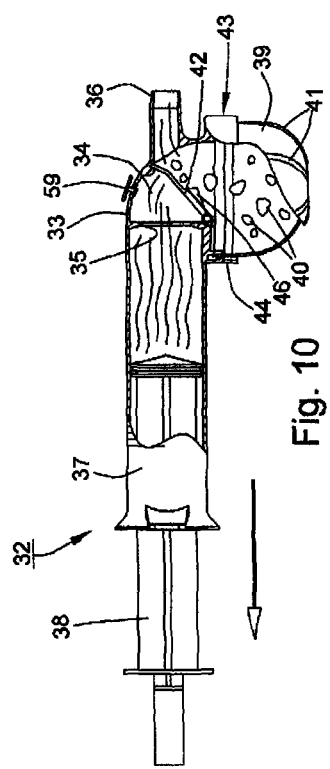

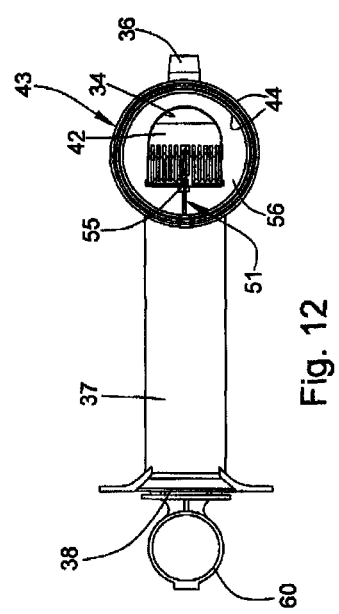
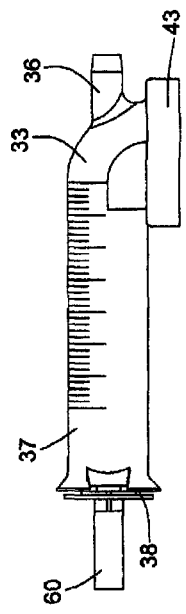
Fig. 12
Fig. 11

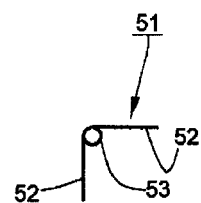
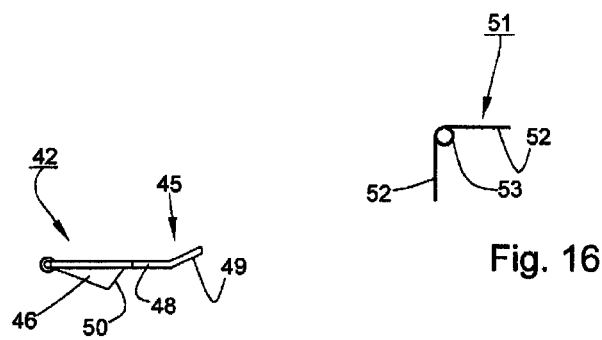
Fig. 16
Fig. 15
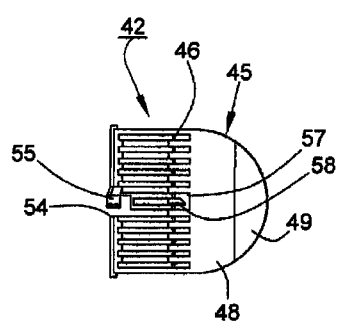
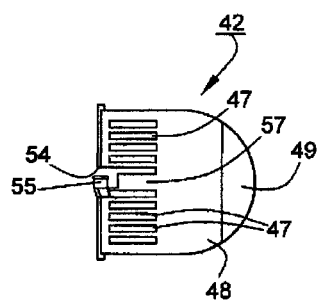
Fig. 13      Fig. 14

BLADDER EVACUATION SYSTEM

This invention relates to a bladder evacuation system.

As described, for example, in U.S. Pat. No. 7,172,579, various types of evacuation systems have been known for irrigating and aspirating body cavities, such as a bladder, during various procedures. One of the problems associated with these systems is that they are cumbersome to use for left-handed surgeons. In addition, these systems rely upon a user squeezing and releasing a pump bulb to irrigate and aspirate a body cavity. Depending on the hand strength of the surgeon, more or less irrigating fluid is dispensed.

Accordingly, it is an object of the invention to provide an evacuation system that can be used be a left-handed or right-handed surgeon.

It is another object of the invention to provide an evacuation system that is easy to use.

Briefly, the invention is directed to a bladder evacuation system comprised of a housing having a cavity, an inlet communicating with the cavity for passage of fluid therebetween and an exit port opposite the inlet and communicating with the cavity for passage of fluid therebetween; means for selectively expelling a fluid through the inlet into the cavity and drawing fluid from the cavity through the inlet; and a container removably secured to the housing in communication with the cavity.

A tube of conventional type has a proximal end in communication with the exit port and a distal end for communication with a bladder of a patient.

In use, the bladder evacuation system selectively delivers fluid to the bladder of a patient and withdraws fluid from the bladder.

In accordance with the invention, a screen is mounted in the cavity of the housing to screen out particulate matter from the return flow of fluid from a bladder for depositing into the container. To this end, the screen is movable between a first position disposed over the container and out of a flow path for the fluid between the inlet and the exit port and a second position disposed across this flow path. In response to passage of fluid in the flow path from the inlet to the exit port, the screen is moved into the first position to allow fluid to pass through the flow path and, in response to drawing of fluid from the cavity through the inlet, the screen is moved into the second position to allow fluid from the exit port to be drawn into the cavity and the inlet while screening particulate matter therefrom for depositing into the container.

In one embodiment, the housing of the bladder evacuation system includes a cylinder that extends longitudinally from the inlet to the cavity and the means for expelling/drawing fluid includes a piston reciprocally mounted in the cylinder. In this embodiment, the housing may be molded as one piece with the cylinder integrated therein.

In another embodiment, the means for expelling/drawing fluid includes a syringe having a cylinder in communication with the inlet of the housing and a piston reciprocally mounted in the cylinder for selectively expelling a fluid therefrom and drawing in fluid thereto. In this embodiment, the syringe and cylinder thereof is made separate from the housing. In addition, housing serves as a lid for receiving the collection container and the screen.

The container is constructed to receive particulate material collected from a bladder or other body cavity. The container may also have a removable collection bag for receiving the particulate material.

Typically, the piston of each embodiment is used to irrigate a bladder during a procedure and to remove fluid and particulate matter from the bladder. That is, a surgeon, while holding the evacuation system in one hand, uses a second hand to reciprocate the piston to effect irrigation and removal.

The system employs a spring that is mounted in the housing for biasing the screen from the first position into the second position. In this respect, the spring has a strength that allows the force of the fluid flow expelled via the piston for irrigating a bladder to push the screen from the second position out of the path of flow and into the first position across the container.

In use, in response to movement of the piston to expel fluid from the cylinder, the screen is moved into the first position to allow fluid to pass into the tube to a bladder and in response to movement of the piston to draw fluid from the tube, the screen is moved into the second position to allow fluid from the tube to pass through while screening particulate matter therefrom for depositing into the container. When the piston is again used to expel fluid into the tube and, thus, a patient, the screen moves into the first position allowing the particulate material collected thereon to fall under gravity into the container.

These and other objects and advantages will be more apparent from the following detailed description taken in conjunction with the accompanying drawings wherein:

FIG. 1 illustrates a side view of a bladder evacuation system in accordance with the invention;

FIG. 2 illustrates a partial cross-sectional view of the evacuation system of FIG. 1;

FIG. 3 illustrates a partial cross-sectional view of the evacuation system of FIG. 1 during movement of the piston into the syringe cylinder;

FIG. 4 illustrates a partial cross-sectional view of the evacuation system of FIG. 1 during withdrawal of the piston from the syringe cylinder;

FIG. 5 illustrates a view of the screen used in the evacuation system of FIG. 1;

FIG. 6 illustrates a side view of the screen of FIG. 5;

FIG. 7 illustrates a perspective view of the spring for biasing the screen;

FIG. 8 illustrates a side view of the spring of FIG. 7;

FIG. 9 illustrates a partial cross-sectional view of a second embodiment of an evacuation system during expelling of fluid in accordance with the invention;

FIG. 10 illustrates a partial cross-sectional view of the embodiment of FIG. 9 during aspiration of fluid in accordance with the invention;

FIG. 11 illustrates a side view of the embodiment of FIG. 9 without the collection container in place;

FIG. 12 illustrates a bottom view of the embodiment of FIG. 9 with the screen in the position of FIG. 10;

FIG. 13 illustrates a top view of the screen in accordance with the invention;

FIG. 14 illustrates a bottom view of the screen of FIG. 13;

FIG. 15 illustrates a side view of the screen of FIG. 13; and

FIG. 16 illustrates a side view of the spring for biasing the screen.

Referring to FIGS. 1 and 2, the bladder evacuation system 10 includes a collection container 11, a tube 12, a syringe 13 and a screen 14.

The collection container 11 is constructed to receive particulate material collected from a bladder or other body cavity. The container 11 may also have a removable collection bag for receiving the particulate material.

The collection container 11 includes a cup-shaped body 15 and a lid 16 that is removably secured to the body 15.

The cup-shaped body 15 may be made of plastic or any other suitable material for the collection of particulate material from a bladder or other body cavity and has a graduated scale 17 thereon for measuring the fluid contents of body 15.

Referring to FIG. 2, the lid 16 is of dome-like shape to define a cavity and to fit over the body 15 and to be secured thereon, for example, in a snap-fit manner. As illustrated, the lid 16 has a peripheral collar 18 formed of two annular flanges 19 that form an annular recess to receive the periphery of the body 15. In an alternative embodiment, the lid 16 may be threaded onto the body 15.

The lid 16 is formed with an inlet 20 shaped to receive a distal end of the syringe 13 and to communicate with the cavity for passage of fluid therebetween as well as with an exit port 21 opposite the inlet 20 and communicating with the cavity for passage of fluid therebetween. The exit port 21 also receives a proximal end of the tube 12. As illustrated, the inlet 20 has a tubular portion 22 that extends radially outwardly of the lid 16 to form a sleeve-like recess for receiving the syringe 13.

The screen 14 is mounted in the lid 16 to be movable between a first position disposed over the body 15, as indicated in FIG. 3, out of a flow path between the inlet 20 and exit port 21 and a second position, as indicated in FIG. 4, disposed across the flow path between the inlet 20 and exit port 21.

As illustrated in FIGS. 2 and 6, the screen 14 is in the form of a plate having a main flat section 23 and an angled section 24 extending at an acute angle from the main section 23. Also, as illustrated in FIG. 5, the main section 23 has a plurality of slots 25. The slots 25 are disposed in three groups with one group of parallel slots adjacent the left end, as viewed, of the screen 14 and two laterally spaced apart groups of slots adjacent the angled section 24.

As indicated in FIG. 2, a spring 26 is mounted in the lid 16 for biasing the screen 14 from the first position (FIG. 3) into the second position (FIG. 4).

Referring to FIGS. 7 and 8, the spring 26 is of U-shape with two coiled ends 27 for mounting of the spring 25 on suitable studs (not shown) within the lid 16 to function as a torsion spring.

Referring to FIG. 2, the syringe 13 serves as means for selectively expelling a fluid through the inlet 20 into the cavity within the lid 16 and drawing fluid from the cavity through the inlet 20. The syringe 13 is of conventional type with a cylinder 28 and a piston 29 and is filled with a fluid suitable for irrigating a bladder or other body cavity.

The cylinder 28 of the syringe 13 slidably fits into the tubular portion 22 of the port 20 in the lid 16 and has a nozzle-like distal end 30 that fits into the remainder of the port 20 to communicate with the container 11 and the proximal end of the tube 12. The cylinder 28 also has a graduated scale 31 thereon for measuring the fluid contents of the syringe 13.

The piston 29 is reciprocally mounted in the cylinder 28 for selectively expelling a fluid therefrom into the tube 12, and, thus, a patient and drawing in fluid thereto from the patient.

Typically, the syringe 13 is use to irrigate a bladder during a procedure and to remove fluid and particulate matter from the bladder after irrigation. That is, a surgeon, while holding the evacuation system 10 in one hand, uses a second hand to reciprocate the piston 29 of the syringe 13 to effect irrigation and removal of fluid and particulate material.

The use of the syringe 13 allows a surgeon to deliver a predetermined amount of fluid for irrigation purposes with each stroke of the piston 27. For example, using a syringe with a capacity of 60 cc, the surgeon can deliver precise amounts of fluid for irrigating up to 60 cc. Further, with the container 11 having a body 15 that is provided with a graduated scale, the surgeon can determine the amount of irrigating fluid introduced into a patient, the amount removed from the patient and the amount remaining in the patient. Typically, the container 11 has a capacity for receiving fluid that is less than the capacity of the syringe 13.

Referring to FIG. 3, during a procedure, a surgeon using a right hand or left hand to hold the evacuation system 10 may employ his/her other hand to push the piston 29 into the cylinder 28 to force a flow of fluid through the nozzle-like distal end 30 of the syringe 13 and the port 20 directly into the oppositely disposed port 21 and tube 12 while moving the screen 14 out of the flow path and downwardly, as viewed, toward the cup-shaped body 15 of the container 11. When the flow of fluid ceases, the spring 26 biases the screen 14 back to the position shown in FIG. 2.

Of note, the spring 26 has a strength that allows the force of the fluid flow expelled from the syringe 13 for irrigating a bladder to push the screen 14 from the position of FIG. 4 out of the path of flow and into the position of FIG. 3 across the container 11.

Referring to FIG. 4, in order to aspirate a bladder, the piston 29 is pulled out of the cylinder 28 to withdraw fluid and particulate material from the bladder and tube 12. During this time, some of the flow of fluid passes through the screen 14 back into the syringe 13 and some of the flow of fluid is deflected by the solid portions of the screen 14 into the cup-shaped body 15 of the container. In addition, particles of particulate matter that are larger than the slots 25 in the screen 14 are screened out of the flow to the syringe 13 and collected on the screen 14 and/or passed into the body 15 of the container 11.

When the piston 29 is again used to expel fluid into the tube 21 and, thus, a patient, the screen 14 moves into the position of FIG. 3 allowing the particulate material collected thereon to fall under gravity into the body 15 of the container 11.

Referring to FIG. 9, wherein like reference characters indicate like parts as above, in a second embodiment, the bladder evacuation system 32 includes a housing 33 having a cavity 34, an inlet 35 communicating with the cavity 34 for passage of fluid therebetween, an exit port 36 opposite the inlet 35 and communicating with the cavity 34 for passage of fluid therebetween and a cylinder 37 extending longitudinally from the inlet 34 in a direction away from the exit port 36. As such, the housing 33 is of one-piece construction as indicated in FIG. 11, for example, being molded of plastic.

The bladder evacuation system 32 also includes a piston 38 that is reciprocally mounted in the cylinder 37 to form a means therewith for selectively expelling a fluid through the inlet 35 into the cavity 34 as indicated in FIG. 9 and drawing fluid from the cavity 34 through the inlet 35 as indicated in FIG. 10.

In addition, a container 39 is removably secured to the housing 33 in communication with the cavity 34 to receive particulate material 40 evacuated from a bladder. This container 39 is of hemispherical shape or other bowl-shape and may be provided with external ribs 41 for ergonomic purposes.

As above, a screen 42 is mounted in the cavity 34 of the housing 33 to be movable between a first position disposed over the container and out of a flow path for the fluid between the inlet 35 and the exit port 36, as indicated in FIG. 9, and a second position disposed across the flow path for the fluid between the exit port 36 and the inlet 20, as indicated in FIG. 10. Thus, in response to movement of the piston 38 to expel fluid from the cylinder 37 and into the cavity 34, the screen 42 is moved into a first position to allow fluid to pass through the flow path to the exit port 36. In response to movement of the piston 38 to draw fluid from the cavity 34 into the cylinder 37, the screen 42 is moved into the second position to allow fluid from the exit port 36 to be drawn into the cavity 34 and inlet 35 while screening particulate matter 40 therefrom for depositing into the container 39.

Referring to FIG. 11, the housing 33 has a peripheral collar 43 formed of two annular flanges 44 (see FIGS. 10 and 12) that are of different lengths to form an annular recess to receive the periphery of the container 39. In addition, the longer flange 44 of the collar 43 is internally threaded to receive an external thread on the container 39 (not shown).

Referring to FIG. 12, the screen 42 has a shape complementary to the cavity 34 to pivot within the cavity 34 with a slight clearance from the internal surface of the cavity 34.

Referring to FIGS. 13 to 15, the screen 42 includes a distal flap portion 45 and a plurality of parallel walls 46 that extend proximally from the flap portion 45 and define slots 47 (see FIG. 14) therebetween for passage of fluid therethrough.

As indicated in FIG. 15, the flap portion 45 has a main flat section 48 and an angled section 49 extending at an acute angle from the main section 48.

Also, as indicated in FIG. 15, each wall 46 has a distal face 50 extending at an obtuse angle from the main section 48 of the flap portion 45, i.e. at an angle greater than 90°. The beveled surfaces of the walls 46 provide a greater surface area for particulate material to impinge on and to be deflected out of the fluid flow during aspiration of a bladder. In addition, sharp corners are avoided which might otherwise trap particles in place thereby leading to a clogging of the slots 47 between the walls 46.

Referring to FIG. 12, a spring 51 is mounted in the housing 33 for biasing the screen 42 from said first position (FIG. 9) into the second position (FIG. 10).

Referring to FIG. 16, the spring 51 is of one piece construction with a pair of legs 52 normally disposed at a right angle to each other and an intermediate coil 53.

Referring to FIGS. 13 and 14, the screen 42 has a slot 54 and tab 55 at a centermost position on one side that are sized to receive the coil 53 of the spring 51 as indicated in FIG. 12. That is, the coil 53 fits into the slot 54 and is received about the tab 55. When in place, one leg 52 of the spring 51 lays on a flat surface 56 that peripherally surrounds the cavity 34 while the other leg 52 lays against an elongated abutment 57 of the screen 42 located centrally of the walls 46. As indicated in FIG. 13, the abutment 57 has a groove 58 to receive the leg 52 of the spring 51.

When the spring 51 is in place, as indicated in FIG. 12, the legs 52 of the spring 51 are splayed outwardly of each other and are, thus, biased towards each other.

Referring to FIG. 10, the housing 33 may be provided with a vent valve 59 that may be operated manually to allow venting of air trapped in the cavity 35 of the housing 33.

The evacuation system 32 is used in the same way as the first embodiment. That is, when fluid is required for a bladder, the piston 38 is moved into the cylinder 37 to deliver fluid through the exit port 36 while, at the same time, pressuring the screen 42 to pivot out of the way and into the position of FIG. 9. As indicated, the piston 38 is provided with a ring-shaped finger hold 60 to facilitate use by the user.

When fluid is to be aspirated from a bladder, the piston 38 is withdrawn from the cylinder thereby drawing a fluid flow from the exit port 36 through the cavity 34 and through the inlet 35. At the same time, the spring 50 biases the screen 42 from the position of FIG. 9 into the position of FIG. 10 to lie across the path of flow of liquid. Any particulate material 40 in the flow thus impinges on the flap portion 45 and the walls 46 of the screen 42 and is deflected downwardly as viewed in FIG. 10.

The irrigation/aspiration of a bladder may be repeated one or more times.

After completion of a procedure, the container may be removed from the housing 33 by unthreading so that the particulate material 40 collected in the container 39 may be pathologically analyzed or otherwise tested. Any standard procedure may be used to encase the otherwise open container 39 for testing.

The invention thus provides an evacuation device that may be manipulated by a right-handed person or a left-handed person.

The invention further provides an evacuation system that can be easily used to irrigate and aspirate a body cavity during a procedure.

What is claimed is:

1. A bladder evacuation system comprising
a housing having a cavity, an inlet communicating with said cavity for passage of fluid therebetween and an exit port opposite said inlet and communicating with said cavity for passage of fluid therebetween;
means for selectively expelling a fluid through said inlet into said cavity and drawing fluid from said cavity through said inlet;
a container removably secured to said housing in communication with said cavity; and
a screen mounted in said cavity of said housing, said screen being movable between a first position disposed over said container and out of a flow path for the fluid between said inlet and said exit port and a second position disposed across said flow path whereby in response to passage of fluid in said flow path from said inlet to said exit port, said screen is moved into said first position to allow fluid to pass through said flow path and in response to drawing of fluid from said cavity through said inlet, said screen is moved into said second position to allow fluid from said exit port to be drawn into said cavity and said inlet while screening particulate matter therefrom for depositing into said container.

2. A bladder evacuation system as set forth in claim 1 further comprising a tube having a proximal end in communication with said exit port and a distal end for communication with a bladder of a patient.

3. A bladder evacuation system as set forth in claim 1 wherein said housing includes a cylinder extending longitudinally from said inlet and said means includes a piston reciprocally mounted in said cylinder.

4. A bladder evacuation system as set forth in claim 1 wherein said means includes a syringe having a cylinder in communication with said inlet of said housing and a piston reciprocally mounted in said cylinder for selectively expelling a fluid therefrom and drawing in fluid thereto.

5. A bladder evacuation system as set forth in claim 1 wherein said screen has a plurality of slots therein.

6. A bladder evacuation system as set forth in claim 1 wherein said screen has a shape complementary to said cavity and includes a distal flap portion and a plurality of parallel walls extending proximally from said flap portion and defining slots therebetween for passage of fluid therethrough.

7. A bladder evacuation system as set forth in claim 6 wherein at least some of said walls have a distal face extending at an obtuse angle from said flap portion.

8. A bladder evacuation system as set forth in claim 1 further comprising a spring mounted in said housing for biasing said screen from said first position into said second position.

9. A bladder evacuation system comprising
a container;
a tube having a proximal end in communication with said container and a distal end for communication with a bladder of a patient;
a syringe having a cylinder in communication with said container and said proximal end of said tube and a piston reciprocally mounted in said cylinder for selectively expelling a fluid therefrom and drawing in fluid thereto; and
a screen mounted in said container, said screen being movable between a first position disposed over said container and out of a flow path for the fluid in said syringe between said syringe and said proximal end of said tube and a second position disposed across said flow path whereby in response to movement of said piston to expel fluid from said cylinder, said screen is moved into said first position to allow fluid to pass through said flow path into said tube and in response to movement of said piston to draw fluid form said tube into said cylinder, said screen is moved into said second position to allow fluid from said tube to be drawn into said cylinder while screening particulate matter therefrom for depositing into said container.

10. A bladder evacuation system as set forth in claim 9 wherein said screen has a plurality of slots therein.

11. A bladder evacuation system as set forth in claim 9 wherein said screen is pivotally mounted between said first position and said second position.

12. A bladder evacuation system as set forth in claim 9 further comprising a spring mounted in said container for biasing said screen from said first position into said second position.

13. A bladder evacuation system comprising
a housing having a cavity, an inlet communicating with said cavity for passage of fluid therebetween, an exit port opposite said inlet and communicating with said cavity for passage of fluid therebetween and a cylinder extending longitudinally from said inlet;
a piston reciprocally mounted in said cylinder for selectively expelling a fluid therefrom and drawing in fluid thereto;
a container removably secured to said housing in communication with said cavity; and
a screen mounted in said cavity of said housing, said screen being movable between a first position disposed over said container and out of a flow path for the fluid between said inlet and said exit port and a second position disposed across said flow path whereby in response to movement of said piston to expel fluid from said cylinder and into said cavity, said screen is moved into said first position to allow fluid to pass through said flow path and in response to movement of said piston to draw fluid from said cavity into said cylinder, said screen is moved into said second position to allow fluid from said exit port to be drawn into said cavity and said inlet while screening particulate matter therefrom for depositing into said container.

14. A bladder evacuation system as set forth in claim 13 wherein said screen has a shape complementary to said cavity and includes a distal flap portion and a plurality of parallel walls extending proximally from said flap portion and defining slots therebetween for passage of fluid therethrough.

15. A bladder evacuation system as set forth in claim 14 wherein at least some of said walls have a distal face extending at an obtuse angle from said flap portion.

* * * * *